(12) United States Patent
Bardy (10) Patent No.: US 8,435,208 B2
(45) Date of Patent: May 7, 2013

(54) SUBCUTANEOUS IMPLANTATION INSTRUMENT WITH A SCISSORED DISSECTING TOOL ASSEMBLY AND METHOD OF CONSTRUCTION

(75) Inventor: Gust H. Bardy, Seattle, WA (US)

(73) Assignee: Cardiac Science Corporation, Bothell, WA (US)

( * ) Notice: Subject to any disclaimer, the term of this patent is extended or adjusted under 35 U.S.C. 154(b) by 339 days.

(21) Appl. No.: 12/774,191

(22) Filed: May 5, 2010

(65) Prior Publication Data

US 2010/0217298 A1    Aug. 26, 2010

Related U.S. Application Data

(60) Division of application No. 11/484,084, filed on Jul. 10, 2006, now Pat. No. 7,736,330, which is a continuation-in-part of application No. 11/345,617, filed on Feb. 1, 2006, now Pat. No. 7,780,625, which is a continuation of application No. 11/025,770, filed on Dec. 20, 2004, now abandoned, which is a continuation of application No. 10/222,719, filed on Aug. 15, 2002, now abandoned.

(51) Int. Cl.
*A61M 31/00* (2006.01)
*A61M 29/00* (2006.01)

(52) U.S. Cl.
USPC .............................. 604/60; 604/106

(58) Field of Classification Search .............. 604/57–65, 604/104–106, 160, 161
See application file for complete search history.

(56) References Cited

U.S. PATENT DOCUMENTS

| | | | |
|---|---|---|---|
| 2,513,014 A | 6/1950 | Fields | |
| 2,830,587 A | 4/1958 | Everett | |
| 3,545,443 A | 12/1970 | Ansari | |
| 4,447,223 A | 5/1984 | Kaye et al. | |
| 4,531,938 A | 7/1985 | Kaye et al. | |
| D295,318 S | 4/1988 | Gazale | |
| 4,769,011 A | 9/1988 | Swaniger | |
| D301,378 S | 5/1989 | Shippert | |
| 4,832,687 A | 5/1989 | Smith, III | |
| 4,900,304 A | 2/1990 | Fujioka et al. | |
| 4,909,250 A | 3/1990 | Smith | |

(Continued)

FOREIGN PATENT DOCUMENTS

| | | |
|---|---|---|
| FR | 2835436 | 8/2003 |
| WO | PCT/US99/08353 | 4/1999 |
| WO | PCT/GB99/02389 | 7/1999 |
| WO | PCT/GB99/029393 | 7/1999 |

*Primary Examiner* — Nicholas Lucchesi
*Assistant Examiner* — Nathan R Price
(74) *Attorney, Agent, or Firm* — Patrick J. S. Inouye; Krista A. Wittman; Leonid Kisselev (57) ABSTRACT

A subcutaneous implantation instrument with a scissored dissecting tool assembly is provided. An incising shaft longitudinally defines a substantially non-circular bore continuously formed to communicatively receive an implantable object and further includes a beveled cutting blade formed on a distal end. A dissecting tool assembly is included. A longitudinally split needle tip forms a pair of blades with cutting edges progressively defined outwardly from the needle tip. A pair of handles are each distally attached to one of the blades and pivotably coupled and disposed for transverse operation, wherein the dissecting tool assembly is removably affixable to the distal end of the incising shaft. A delivery mechanism longitudinally defines a substantially non-circular bore continuously formed to deploy the implantable object into the incising shaft.

6 Claims, 11 Drawing Sheets

U.S. PATENT DOCUMENTS

| | | |
|---|---|---|
| 4,915,686 A | 4/1990 | Frederick |
| 4,936,827 A | 6/1990 | Grimm et al. |
| 4,941,874 A | 7/1990 | Sandow et al. |
| 4,950,234 A | 8/1990 | Fujioka et al. |
| 5,250,026 A | 10/1993 | Ehrlich et al. |
| 5,273,532 A | 12/1993 | Niezink et al. |
| 5,279,554 A | 1/1994 | Turley |
| 5,279,555 A | 1/1994 | Lifshey |
| 5,284,479 A | 2/1994 | De Jong |
| 5,300,106 A | 4/1994 | Dahl et al. |
| 5,304,119 A | 4/1994 | Balaban et al. |
| 5,331,966 A | 7/1994 | Bennett et al. |
| 5,358,474 A | 10/1994 | Kaldany |
| 5,405,324 A | 4/1995 | Wiegerinck |
| 5,484,403 A | 1/1996 | Yoakum et al. |
| 5,501,664 A | 3/1996 | Kaldany |
| 5,501,672 A | 3/1996 | Firth et al. |
| 5,507,807 A | 4/1996 | Shippert |
| 5,526,772 A | 6/1996 | Curkendall |
| 5,558,637 A | 9/1996 | Allonen et al. |
| 5,562,613 A | 10/1996 | Kaldany |
| 5,669,890 A | 9/1997 | Grimm |
| 5,772,671 A | 6/1998 | Harmon |
| D396,287 S | 7/1998 | Morales |
| 5,810,769 A | 9/1998 | Schlegel et al. |
| 5,827,293 A | 10/1998 | Elliot |
| 5,908,404 A | 6/1999 | Elliot |
| 5,944,732 A | 8/1999 | Raulerson et al. |
| 5,984,890 A | 11/1999 | Gast et al. |
| 6,190,350 B1 | 2/2001 | Davis et al. |
| 6,230,059 B1 | 5/2001 | Duffin |
| 6,245,052 B1 | 6/2001 | Orth et al. |
| 6,261,243 B1 | 7/2001 | Burney et al. |
| 6,293,925 B1 | 9/2001 | Safabash et al. |
| 6,317,626 B1 | 11/2001 | Warman |
| 6,488,649 B1 | 12/2002 | Lichten |
| 6,551,289 B1 | 4/2003 | Higuchi et al. |
| 6,682,480 B1 | 1/2004 | Habib et al. |
| 6,761,725 B1 | 7/2004 | Grayzel et al. |
| 7,247,160 B2 | 7/2007 | Seiler et al. |
| 7,736,330 B2 * | 6/2010 | Bardy ............................ 604/57 |
| 2003/0135153 A1 | 7/2003 | Hagemeier |

* cited by examiner

SUBCUTANEOUS IMPLANTATION INSTRUMENT WITH A SCISSORED DISSECTING TOOL ASSEMBLY AND METHOD OF CONSTRUCTION

CROSS-REFERENCE TO RELATED APPLICATIONS

This patent application is a divisional application of U.S. Pat. No. 7,736,330, issued Jun. 15, 2010; which is a continuation-in-part application of U.S. Pat. No. 7,780,625, issued on Aug. 24, 2010; which is a continuation of U.S. patent application, Ser. No. 11/025,770, filed Dec. 20, 2004, abandoned; which is a continuation of U.S. Pat. No. 6,436,068, issued Aug. 20, 2002, the priority dates of which are claimed and the disclosures of which are incorporated by reference.

FIELD

The present invention relates in general to subcutaneous implantation instruments and methods and, in particular, to a subcutaneous implantation instrument with a scissored dissecting tool assembly and method of construction.

BACKGROUND

Health care assessment includes the review and analysis of physiometry collected and recorded by electronic data sensors. The type and quality of physiometry can depend upon the type and location of sensor used. External sensors, such as thermometers, blood pressure cuffs, heart rate monitors, and the like, are limited in the kinds of information, which they are able to collect, and can encumber the patient. Implantable in situ sensors can provide a direct stream of recorded physiometry, but are invasive and require surgical implantation.

Recent advances in microchip technology have created a new generation of highly integrated, implantable sensors and medical devices, such as implantable cardioverter defibrillators, pacemakers, and insertable loop recorders. For instance, PCT Application Nos. PCT/GB99/02389, to Habib et al., filed Jul. 22, 1998, pending, and PCT/GB99/02393, to Habib et al., filed Jul. 22, 1998, pending, respectively describe an implantable sensor chip and treatment regiment, the disclosures of which are incorporated by reference. Each sensor chip can collect and transmit physiometric data by wireless telemetry to a receiver external to a body. Similarly, the emerging Bluetooth wireless communication standard, described at http://www.bluetooth.com/developer/specification/specification.asp, proposes a low cost, small form factor solution for short range data communications, potentially suitable for use in implantable sensor technology.

Nevertheless, microchip sensors must still be implanted via some form of surgical procedure. Minimally invasive implantation using large bore needles or flat-edged blades is impracticable because sensors, particularly when embodied using microchip technology, favor a prismatic shape with substantially rectangular cross sections that are incompatible with circular bores. As well, large bore needles can core out flesh, skin, or hide, when used in animals, as the instruments are inserted subcutaneously, which creates a risk of infection. Moreover, wider-tipped instruments, such as a hollow point chisel, can potentially cause tearing, gouging, or similar injury due to the width of the cutting edge.

In addition, although current surgical implantation approaches attempt to minimize the size of incision and degree of invasiveness, implantation is, at best, costly, time-consuming, traumatic, requires multiple instruments and maneuvers, and potentially risky to the patient. For example, anesthetizing is conventionally performed using a topical or local anesthetic agent on the implantation site.

Subcutaneous implantable sensors offer the best compromise between in situ sensors and external sensors and are potentially insertable with a simple injection, rather than surgical procedure. These sensors are typically implanted below the dermis in the layer of subcutaneous fat. Several approaches to the subcutaneous implantation of solid materials have been described.

An insertion and tunneling tool for a subcutaneous wire patch electrode is described in U.S. Pat. No. 5,300,106, to Dahl et al., issued Apr. 5, 1994. The tunneling tool includes a stylet and a peel-away sheath. The tunneling tool is inserted into an incision and the stylet is withdrawn once the tunneling tool reaches a desired position. An electrode segment is inserted into the subcutaneous tunnel and the peel-away sheath is removed. Although providing a tool for subcutaneous implantation, the Dahl device requires an incision into the subcutaneous fat layer and forms an implantation site larger than the minimum sized required by the electrode segment. Further more, the cylindrical bore precludes the injection of non-conforming solid sensors or materials.

An implant system for animal identification that includes a device for implanting an identification pellet in a fat layer beneath the hide or skin of an animal is described in U.S. Pat. No. 4,909,250, to Smith, issued Mar. 20, 1990. The device includes a curved needle-like tube that terminates at a tapered, sharpened point. An elongated, flexible plunger is slidably received within the needle-like tube. The pointed tip is inserted through the hide or skin and the plunger is actuated to drive the identification pellet from the tip into the fat layer. However, the Smith device uses an oversized open bore which can cause coring of the hide or flesh.

A trocar for inserting implants is described in PCT Application No. PCT/US99/08353, to Clarke et al., filed Oct. 29, 1999, pending. An implant retention trocar includes a cannula for puncturing the skin of an animal and an obturator for delivering the implant. A spring element received within the cannula prevents an implant from falling out during the implant process. The cannula has a distal tip design which causes a minimum of trauma and tearing of tissue during implant insertion. However, the distal tip design is specifically directed to cannulas having a substantially circular bore and thereby limits the size and shape of implant which can be inserted through the Clarke trocar.

An instrument for injecting implants through animal hide is described in U.S. Pat. No. 5,304,119, to Balaban et al., issued Apr. 19, 1994. The instrument includes an injector having a tubular body divided into two adjacent segments with a hollow interior bore. A pair of laterally adjacent tines extend longitudinally from the first segment to the distal end of the tubular body. A plunger rod has an exterior diameter just slightly larger than the interior diameter of the tubular body. With the second segment inserted beneath the animal hide, the push rod is advanced longitudinally through the tubular body, thereby pushing the implant through the bore. As the implant and rod pass through the second segment, the tines are forced radially away from each other, thereby dilating or expanding the incision, and facilitating implant. The instrument is removed from the incision following implantation. Though avoiding the coring of animal hide or flesh, the instrument forms an implantation site larger than the minimum sized required by the implant and causes potentially damaging compaction of the implant against the laterally adjacent tines during implant delivery.

Therefore, there is need for a non-surgical instrument and method for subcutaneous implantation of sensors and solid materials that preferably does not require an incision preparatory to instrument insertion.

There is a further need for a subcutaneous implantation instrument and method capable of implanting sensors and other solid materials that are not readily disposed to implantation through a substantially circular bore.

Moreover, there is a further need for a subcutaneous implantation instrument and method which is minimally invasive, preferably creating the smallest needed implantation site, and capable of implantation without exposing the implant to longitudinal stresses.

There is a still further need for an implantation instrument that provides a progressive widening of an implantation site. Such progressive widening would facilitate the use of wider-tipped instruments that provide sufficient girth to admit implantable sensors and medical devices with lowered patient trauma. Preferably, such an instrument would include provision for application of an anesthetic agent.

SUMMARY

An implantation instrument and method of use for implanting sensors and other solid materials in a subcutaneous or other site is provided. As used herein, "subcutaneous" refers generally to those implantation sites located within a body below the skin. The implantation instrument consists of an incising shaft attached to a syringe body. The syringe body and incising shaft both define a substantially non-circular hollow bore for accommodating the sensor or solid material. The subcutaneous site is formed by a cutting edge on the distal end of the incising shaft. The subcutaneous site can be cleared using a clearing trocar slidably received within the hollow bore. The sensor or solid material is advanced through the hollow bore and delivered into the subcutaneous site. The depth of the subcutaneous site can be limited using a penetration limiting mechanism.

One embodiment provides a subcutaneous implantation instrument with a scissored dissecting tool assembly. An incising shaft longitudinally defines a substantially non-circular bore continuously formed to communicatively receive an implantable object and further includes a beveled cutting blade formed on a distal end. A dissecting tool assembly is included. A longitudinally split needle tip forms a pair of blades with cutting edges progressively defined outwardly from the needle tip. A pair of handles are each distally attached to one of the blades and pivotably coupled and disposed for transverse operation, wherein the dissecting tool assembly is removably affixable to the distal end of the incising shaft. A delivery mechanism longitudinally defines a substantially non-circular bore continuously formed to deploy the implantable object into the incising shaft.

A further embodiment provides a method for constructing a subcutaneous implantation instrument with a scissored dissecting tool assembly. An incising shaft is fashioned to longitudinally define a substantially non-circular bore continuously formed to communicatively receive an implantable object and to further include a beveled cutting blade formed on a distal end. A dissecting tool assembly is included. A longitudinally split needle tip is provided to form a pair of blades with cutting edges progressively defined outwardly from the needle tip. A pair of handles are included that are each distally attached to one of the blades and pivotably coupled and disposed for transverse operation, wherein the dissecting tool assembly is removably affixable to the distal end of the incising shaft. A delivery mechanism is provided to longitudinally define a substantially non-circular bore continuously formed to deploy the implantable object into the incising shaft.

One principal value of such a subcutaneous implantation instrument and method would be to enable the subcutaneous insertion of implantable objects and devices, such as sensors, without an operating room or special procedures room. In essence, the subcutaneous implantation instrument and method reduce insertion of implantable objects and devices having non-conforming shapes to be the functional equivalent of an injection.

Still other embodiments of the present invention will become readily apparent to those skilled in the art from the following detailed description, wherein is described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

Figure 1:
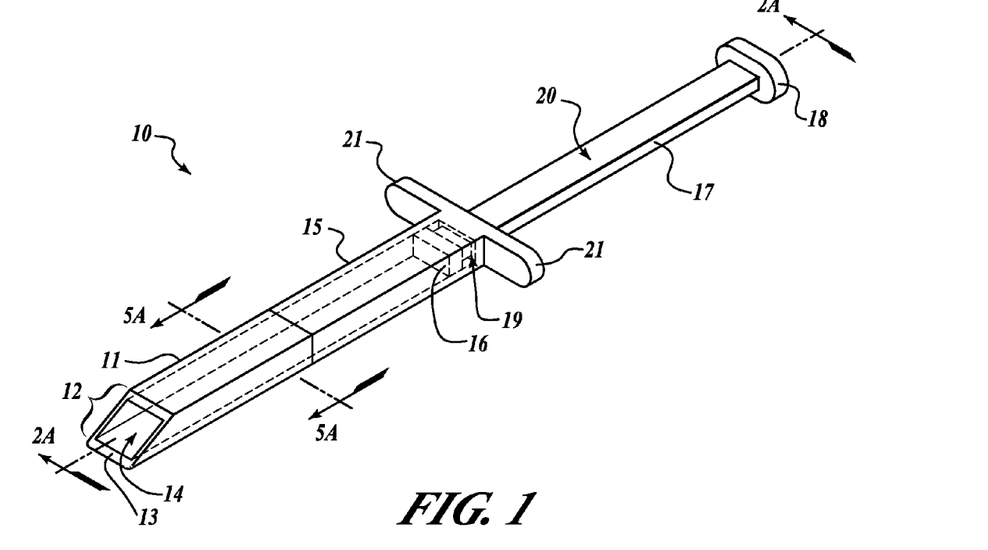
FIG. 1 is a perspective view of an instrument for implanting sensors or solid materials in a subcutaneous or other tissue location in accordance with the present invention.

FIG. 1 is a perspective view of an instrument 10 for implanting objects in a subcutaneous or other tissue location in accordance with the present invention. The implantation instrument 10 consists of two principal groups of components, an incising body consisting of an incising shaft 11 and a syringe body 15, and a delivery assembly consisting of a plunger assembly 20. The instrument 10 can be used to non-surgically implant an object, such as a sensor or monitor, medical therapeutic device, or other solid or semi-solid object. The delivery assembly is received into the syringe body bore by sliding the plunger assembly 20 through proximal bore opening 19. An implantable object is received into the syringe body bore. During an implant procedure, the implantable object is deployed into the incising shaft and thence inserted subcutaneously into an implantation site by progressive distal urging of the plunger assembly 20, as further described below beginning with reference to FIG. 18.

The incising shaft 11 is a hollow point chisel that is formed with a beveled and rounded tip 12 that tapers into a surgically sharp cutting edge 13 formed on a distal edge. The beveled tip 12 includes a distal bore opening 14 through which the implantable object is delivered into the implantation site.

The implantable object includes medical monitoring and diagnostic devices, such as an implantable physiometry sensor, and non-medical monitoring devices, such as an environmental or activity monitor. Such sensors generally record data for subsequent retrieval and can be autonomously triggered or triggered manually by the implant recipient. One implantable sensor microchip suitable for use in the present invention is described in PCT Application No. PCT/GB99/02389, to Habib et al., filed Jul. 22, 1998, pending, the disclosure of which is incorporated by reference. Such a sensor could be used for monitoring and collecting physiological or chemical measures. A further implantable monitoring device suitable for use is the Reveal insertable loop recorder, manufactured by Medtronic, Inc., Minneapolis, Minn., which is an implantable heart monitor for diagnosing the causes of syncope and other transient heart symptoms involving rhythm-related disorders, as described in U.S. Pat. No. 5,331,966, issued Jul. 26, 1994 to Bennett et al; U.S. Pat. No. 6,230,059, issued May 8, 2001 to Duffin; and U.S. Pat. No. 6,317,626, issued Nov. 13, 2001 to Warman, the disclosures of which are incorporated by reference. Other medical monitoring and diagnostic devices are possible.

The implantable object also includes non-sensor-type implantable medical devices, including implantable medical devices for therapeutic uses, such as administering cardiac pacing or rhythm therapy; providing neural, muscle, or organ stimulation; cancer treatment; and delivering or dosing medication. As well, the present invention has equal applicability to implantation of other types of non-medical sensors, including location and identification sensors, such as radio frequency identification (RFID) tags. Such sensors could include data transmitters with which to exchange recorded data and instructional signals.

Finally, the implantable object can include solid or semi-solid materials, such as a gelatinous drug bolus. In one embodiment, the implantable object has approximate dimensions of 5 mm by 10 mm by 20 mm, although other dimensions can be equally suitable. The critical dimension is the cross-sectional profile, that is, the height and width, of the implant, which must conform to passage through the syringe body and incising shaft bores. Other non-linear, prismatic shapes are equally usable provided the implantable object can fit within the confines of the syringe body and incising shaft bores. The implant could also be folded or compacted to minimize the cross-sectional profile with the implant unfolding or expanding upon implantation. As well, the implant is preferably protected against damage by encasement within, for example, a mannitol pellet in the case of a solid drug delivery system or epoxy in the case of an implantable sensor or medical device. Other sizes, shapes, and types of non-liquid implantable objects are possible.

The incising shaft 11 is fixably attached to the syringe body 15 through frictional, adhesive, or preformed constructive means, as is known in the art. Both the incising shaft 11 and syringe body 15 define a substantially non-circular hollow bore extending continuously along a shared longitudinal axis, as further described below with reference to FIGS. 5A-D.

The plunger assembly includes a plunger 16, an interconnecting plunger shaft 17 and a plunger end piece 18. The plunger 16 is conformably shaped to fit within the syringe body bore. The plunger end piece 18 facilitates deployment of the plunger assembly through the syringe body bore and is preferably shaped to fit a thumb or palm impression. In a further embodiment, the non-circular hollow bore opens to the distal end of the incising shaft 11 and extends only partly through to thereby form a cavity, rather than a tube, but with provision for the sliding of the plunger shaft 17.

In the described embodiment, the implantation instrument 10 is designed for inexpensive and disposable use utilizing low-cost, sanitizable materials. The implantation instrument 10 can be used for out-patient or non-surgical subcutaneous implant and insertion of an implantable object, as further described below beginning with reference to FIG. 18. The incising shaft 11 can be fashioned from surgical grade stainless steel and has the approximate dimensions of approximately 10 mm by 5 mm in cross section. The incising shaft 11 is approximately 50 mm long and the length can be varied to accommodate different implantation depths. The plunger 16 is formed from plastic and rubber and preferably forms a watertight seal within the syringe body bore and has the approximate dimensions of approximately 8 mm by 3 mm in cross section. The plunger shaft 17 and plunger end piece 18 are formed from plastic or similar material. Other materials, as would be recognized by one skilled in the art, could be substituted.

In a further embodiment, the syringe body 15 and plunger assembly can be replaced by an automated injection system, such as used with immunization injection guns or similar devices. These devices typically employ compressed air or other inert gases to administer medication in lieu of manual plungers. Other automated variations include spring-loaded and similar mechanical injection systems. The incising shaft 11 is fixably attached to the automated injection system which functions as a delivery mechanism in place of the syringe body 15 and plunger assembly. Thus, the implant would be pushed through the incising shaft bore using the compressed air or gas, or mechanical equivalent.

Figure 2A:
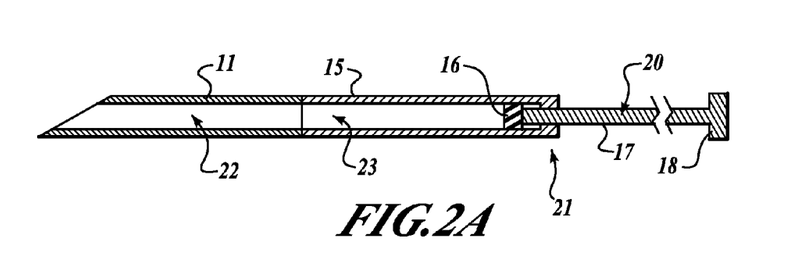
FIG. 2A is a longitudinal cross-sectional view of the implantation instrument with a straight incising shaft.

FIG. 2A is a longitudinal cross-sectional view of the implantation instrument 10 with a straight incising shaft 11. The hollow bore defined by both the incising shaft 11 and the syringe body 15 runs along a common shared axis. The incising shaft bore 22 is sized to allow the implant to advance smoothly into the implantation site under the forward lateral urging of the plunger assembly 20. The syringe body bore 23 must be at least as large as the incising shaft bore 22, but can be slightly larger to accommodate lubricants, anesthetizing agents, or similar coatings, such as mannitol, applied over the implantable object.

The syringe body 15 preferably includes a circular collar 21, pair of winglets, ears, or eyelets, or similar structure, optionally formed on a proximal end of the syringe body 15 to assist a user in depressing the plunger assembly 20.

Figure 2B:
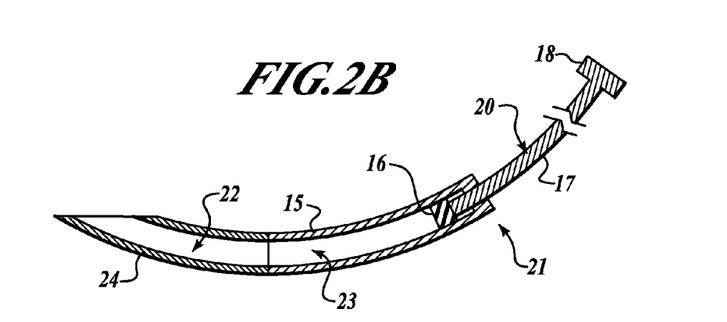
FIG. 2B is a longitudinal cross-sectional view of the implantation instrument with a curved incising shaft.

FIG. 2B is a longitudinal cross-sectional view of the implantation instrument with a curved incising shaft 24. The curved incising shaft 24, as well as the syringe body 15 and related components, are shaped into a substantially continuous curve along the ventral side. The curvature helps regulate the penetration depth of the incising shaft and, in the described embodiment, has an arc of approximately 20 degrees.

Figure 3:
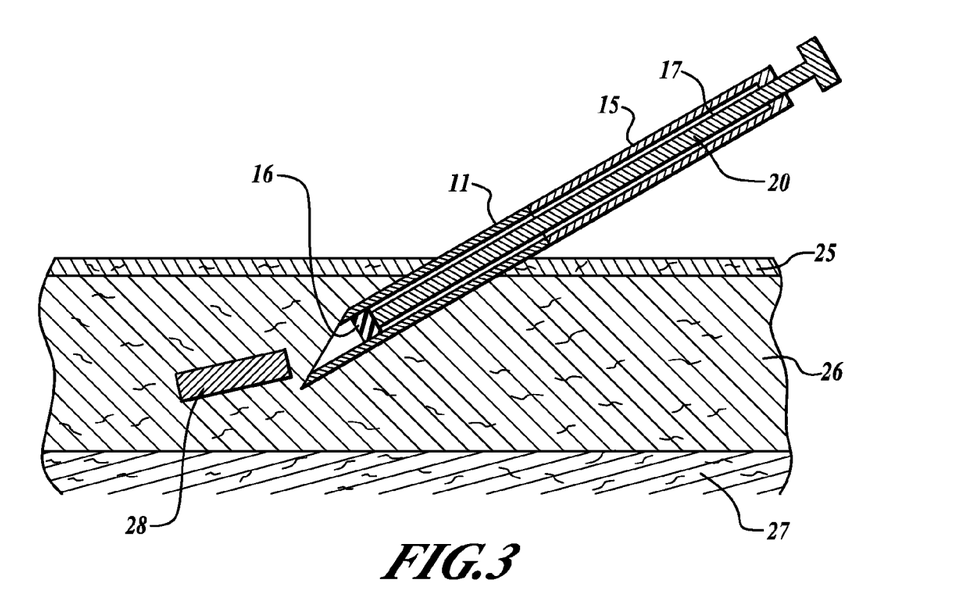
FIG. 3 is a diagrammatic view illustrating the implantation of an object into a subcutaneous site.

FIG. 3 is a diagrammatic view illustrating the implantation of an implantable object 28, including a sensor, implantable medical device, such as an implantable cardioverter defibrillator, pacemaker, or insertable loop recorder, or other solid material into a subcutaneous site. Other implantable objects are possible. During implantation, the incising shaft 11 is inserted through the dermis 25 and guided into the layer of subcutaneous fat 26, above the layer of muscle 27, to a subcutaneous implantation site. The implantable object 28 is fed through the proximal bore opening 19 or received through the distal bore opening of the syringe body 15. The implantable object 28 is then further advanced through the syringe body bore 23 and the incising shaft bore 22 by the plunger 16 into the subcutaneous site. Note that although the foregoing view illustrates an implant into the subcutaneous fat layer, one skilled in the art would appreciate that subcutaneous implantation locations are not strictly limited to the subcutaneous fat layer and are generally termed as those implantation locations situated subdurally within a body under the skin. Accordingly, subcutaneous implantation sites further include locations that are intramuscular and submuscular, or within a body cavity, including intrathoracic.

Figure 4A:
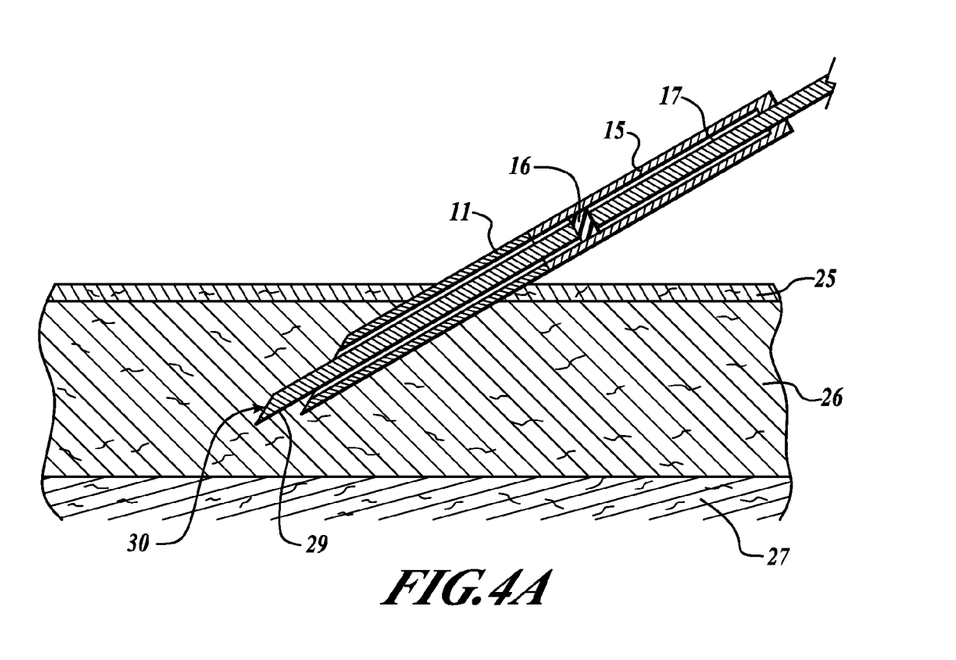
FIG. 4A is a diagrammatic view illustrating the clearing of a subcutaneous site using the implantation instrument fitted with a clearing trocar in accordance with a further embodiment.
Figure 6:
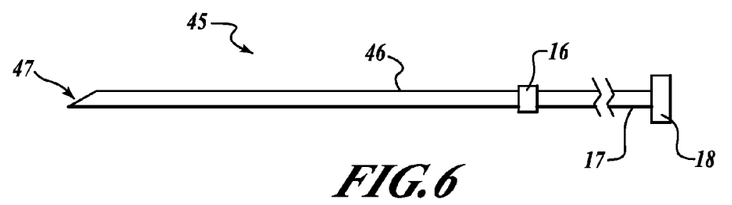
FIG. 6 is a segmented side view of a clearing trocar.

FIG. 4A is a diagrammatic view illustrating the clearing of a subcutaneous site using the implantation instrument 10 fitted with a clearing trocar 29 in accordance with a further embodiment. The clearing trocar 29, as further described below with reference to FIG. 6, is mounted to its own handle or plunger assembly and has a sharp cutting tip 30 for optionally clearing a subcutaneous site prior to delivery of the implant.

Prior to implantation, the clearing trocar 29 is slidably received into the syringe body 15 and is advanced until the cutting tip 30 is even with the proximal bore opening 19 of the incising shaft 11. During operation, the incising shaft 11 and clearing trocar 29 are inserted through the dermis 25 and guided into the layer of subcutaneous fat 26, above the layer of muscle 27.

The cutting edge 13 of the beveled tip 12 makes an entry incision through the dermis 25 and is laterally pushed into the subcutaneous fat 26 until the cutting edge 13 is adjacent to the subcutaneous site. The clearing trocar 29 is then urged through the subcutaneous fat 26 by advancement of its handle or plunger assembly to prepare the implantation site for delivery of the implantable object 28, including an implantable sensor, medical device, or other solid material. The clearing trocar 29 is then withdrawn from the subcutaneous site and out of the implantation instrument 10.

Figure 4B:
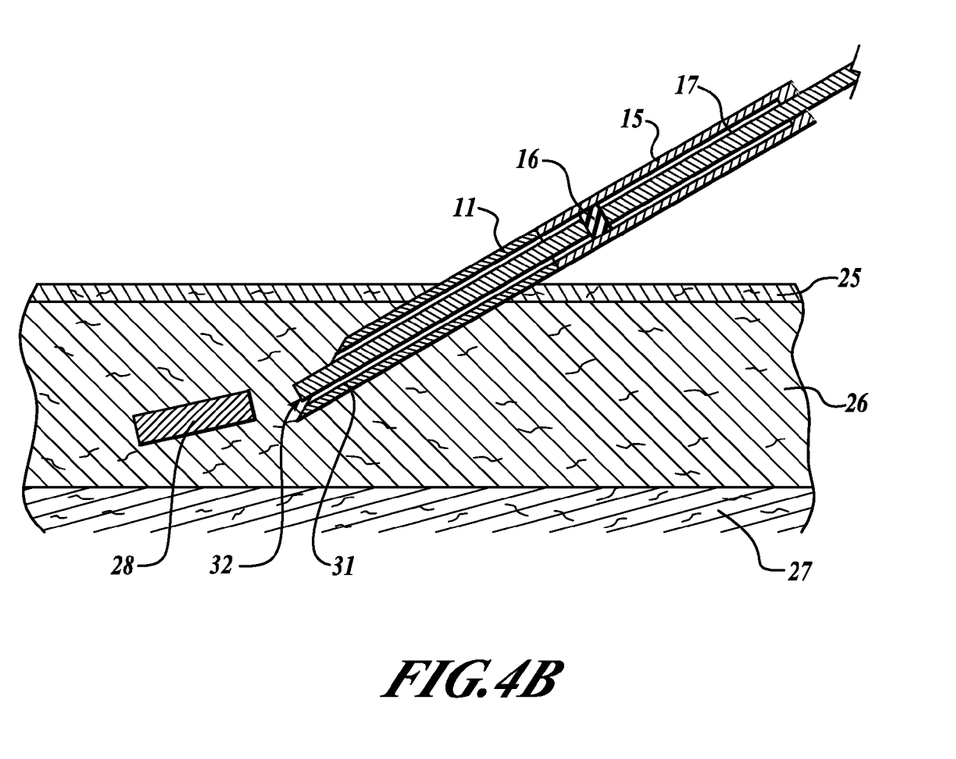
FIG. 4B is a diagrammatic view illustrating the subcutaneous implantation of an object using the implantation instrument fitted with a pushing stylet in accordance with a further embodiment.

FIG. 4B is a diagrammatic view illustrating the subcutaneous implantation of an implantable object 28 using the implantation instrument 10 fitted with a pushing stylet 31 in accordance with a further embodiment. The pushing stylet 31, as further described below with reference to FIG. 7, has a blunt tip 32 for advancing the implantable object 28 through the syringe body bore 23 and incising shaft bore 22 and into the subcutaneous site. The cross section of the pushing stylet 31 closely conforms to the incising shaft bore 22 while the plunger 16 closely conforms to the syringe body bore 23. The pushing stylet 31 thus extends the reach of the plunger assembly 20 and allows the syringe body bore 23 to have a different cross-section than the incising shaft bore 22.

The pushing stylet 31 is used while the incising shaft 11 is in situ in the subcutaneous layer 26. Prior to delivery, the implantable object 28 is fed through the proximal bore opening 19 of the syringe body 15 and further advanced within the syringe body bore 23 by contact with the plunger 16. The pushing stylet 31 is slidably received into the syringe body 15 and is advanced until the blunt tip 32 contacts the implantable object 28. During operation, the implantable object 28 is urged through the incising shaft bore 22 by the pushing stylet 31 and into the subcutaneous site by advancement of the plunger assembly. Upon delivery of the implantable object 28 into the subcutaneous site, the incising shaft 11 and pushing stylet 31 are withdrawn.

Although operation of the implantation instrument 10 is described with reference to the implantation of sensors or solid materials into a subcutaneous site situated within the layer of subcutaneous fat 26, implantations could also be effected in other subcutaneous, intramuscular, intraperitoneal, intrathoracic, intracranial, intrajoint, as well as other organ or non-subcutaneous sites, as would be recognized by one skilled in the art. In addition, the foregoing procedure could be modified to forego the use of the clearing trocar 29 for small implantable objects 28. The clearing effect of the clearing trocar 29 can be approximated by use of the incising shaft 11 alone whereby the incising shaft 11 is inserted into the subcutaneous site and then withdrawn by reverse deployment, thereby forming a slightly overwide implantation site.

The operations of subcutaneous implantation can be carried out over a plurality of sites and with the same or different implantable objects 28. Similarly, several implantable object 28 could be implanted at the same subcutaneous site during a single implantation operation.

Figure 5A:
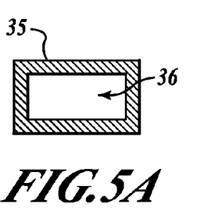
FIGS. 5A-D are transverse cross-sectional views of the implantation instrument illustrating, by way of example, various bore configurations.
Figure 5B:
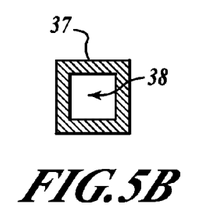
Figure 5C:
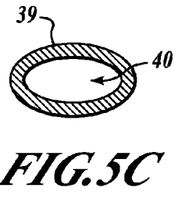
Figure 5D:
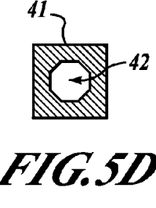

FIGS. 5A-D are transverse cross-sectional views of the implantation instrument 10 illustrating, by way of example, various bore configurations. FIG. 5A illustrates an incising shaft 35 with a substantially rectangular bore 36. FIG. 5B illustrates an incising shaft 37 with a substantially square bore 38. FIG. 5C illustrates an incising shaft 39 with a substantially oval bore 40. And FIG. 5D illustrates an incising shaft 41 with a substantially hexagonal bore 42. Note the circumferential shape of the incising shaft need not follow the internal shape of the incising shaft bore. Other bore configurations, including variations on oval, rectangular, square, pentagonal, hexagonal, heptagonal, octagonal, and similar equilateral or non-equilateral shapes, are feasible.

In the described embodiment, the rectangular bore 36 has the dimensions of approximately 10 mm by 5 mm. The syringe body bore 23 has a length of approximately 5 cm.

FIG. 6 is a segmented side view of a clearing trocar 45. The clearing trocar 45 consists of a beveled tip 47 on the distal end of the clearing trocar 45 and a clearing trocar shaft 46 affixed, either fixably or removably, to the distal end of a plunger 16.

During a clearing operation, the clearing trocar 45 is fully extended from the distal bore opening 14 of the incising shaft 11. The clearing trocar shaft 46 is only long enough to clear out the subcutaneous site. The plunger 16 acts as a stop that limits the extent of penetration of the clearing trocar 45, thereby preventing the clearing trocar 29 from incising too deeply into the subcutaneous fat 29. In addition, the clearing trocar 29 is sized to approximate the girth of the incising shaft bore 22 and will clear a subcutaneous site only as wide as minimally necessary to facilitate implantation of the implantable object. In the described embodiment, the clearing trocar 45 has a length of approximately 2 cm beyond the tip of the syringe body 15.

Figure 7:
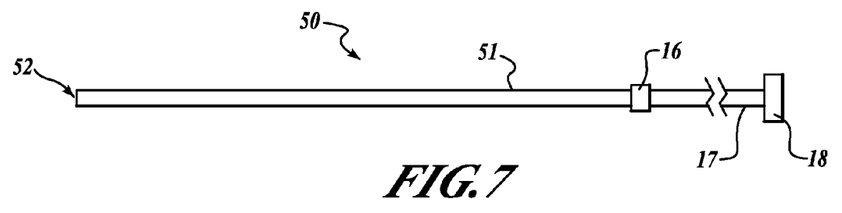
FIG. 7 is a segmented side view of a pushing stylet.

FIG. 7 is a segmented side view of a pushing stylet 50. The pushing stylet 50 consists of a blunt tip 52 on the distal end of the pushing stylet 50 and a pushing stylet shaft 51 affixed, either fixably or removably, to the distal end of a plunger 16.

During a delivery operation, the pushing stylet 50 is extended from the distal bore opening 14 of the incising shaft 11. The pushing stylet shaft 51 is only long enough to clear the distal bore opening 14. The plunger 16 acts as a stop that limits the lateral travel of the pushing stylet 50. In the described embodiment, the pushing stylet 50 has an additional length of approximately 2 cm beyond the tip of the syringe body 15.

Figure 8A:
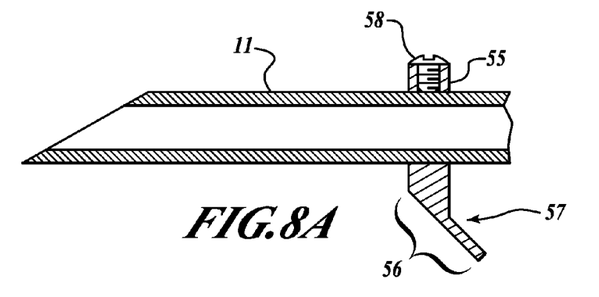
FIGS. 8A-8B are section views illustrating penetration limiting mechanisms for use with the implantation instrument.
Figure 8B:
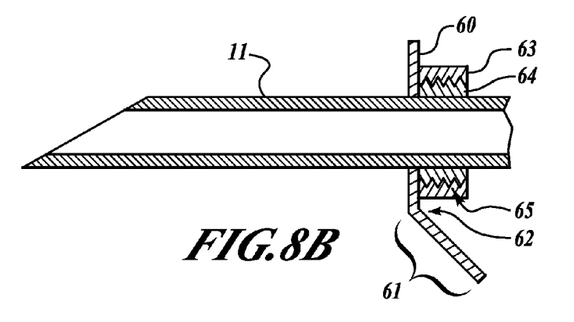

FIGS. 8A-8B are section views illustrating penetration limiting mechanisms for use with the implantation instrument 10. The penetration limiting mechanisms limit the depth of penetration of the incising shaft 11 and help prevent excessive penetration. FIG. 8A shows a fixed penetration limiting mechanism consisting of a stopping flange 55 attached to the incising shaft 11. The position of the stopping flange 55 along the incising shaft 11 can be adjusted by loosening a holddown screw 58 and sliding the stopping flange 55 into the desired location. The lower edge of the stopping flange 55 has a bend 57 with an angle τ, preferably between approximately 30° and 60°, thereby forming an elbow 56 which stops lateral travel upon contact with the skin.

FIG. 8B shows an adjustable penetration limiting mechanism consisting of a stopping flange 60 attached a frictional collar 64. The stopping flange 60 and frictional collar 64 are slidably attached to the incising shaft 11. An adjustable collar 64, preferably in threaded communication 65 with the frictional collar 64, manually stops deployment of the penetration limiting mechanism by tightening the frictional collar 64 against the incising shaft 11. The lower edge of the stopping flange 60 has a bend 62 with an angle υ, preferably between approximately 30° and 60°, thereby forming an elbow 61 which stops lateral travel upon contact with the skin.

Figure 9:
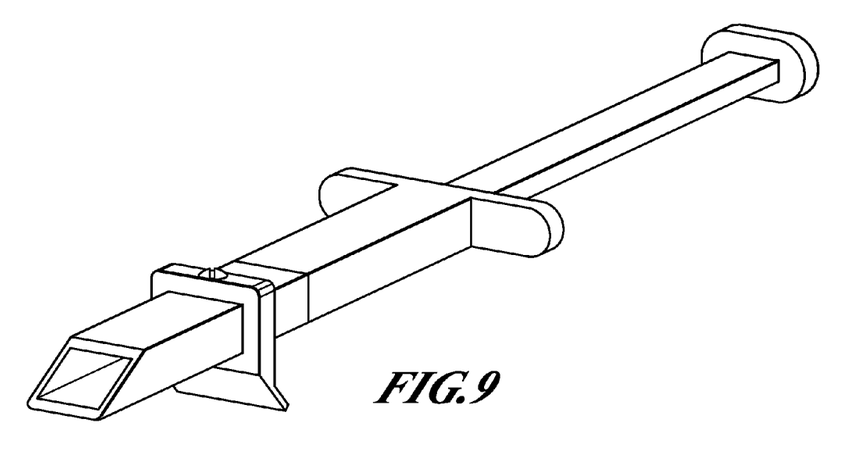
FIG. 9 is a perspective view of an instrument for implanting objects in a subcutaneous or other tissue location in accordance with a further embodiment of the present invention.

FIG. 9 is a perspective view of an instrument for implanting objects in a subcutaneous or other tissue location in accordance with a further embodiment of the present invention. The instrument is equipped with the stopping flange 55 shown in FIG. 8A. Other forms of penetration limiting mechanisms, both fixed and adjustable, could be used, as would be readily apparent to one skilled in the art.

Figure 10A:
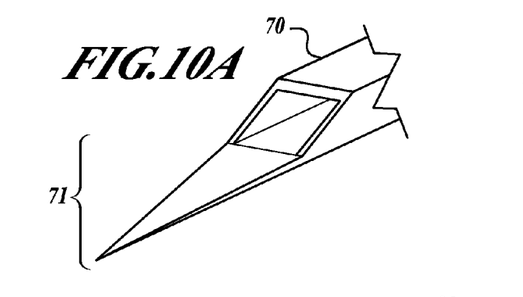
FIGS. 10A-10C are perspective views of cutting edges formed on distal edges of incising shafts, in accordance with further embodiments.
Figure 10B:
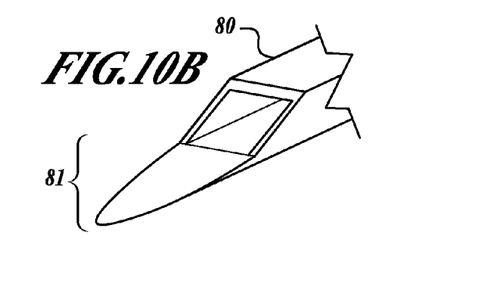
Figure 10C:
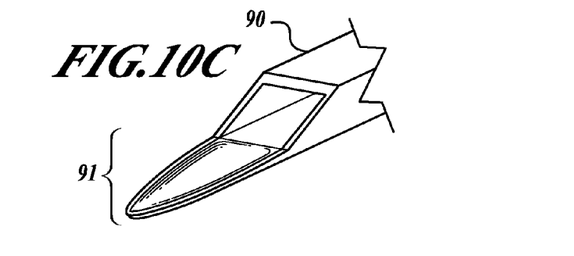

In addition to being flat and chisel-like, the cutting edge of the incising shaft can be shaped as a progressive cutting or clearing blade, or a dissecting tool suitable for use in facilitating subcutaneous insertion. FIGS. 10A-10C are perspective views of progressive cutting edges 71, 81, 91 formed on distal edges of incising shafts 70, 80, 90 in accordance with further embodiments. The cutting edge can be shaped to facilitate subcutaneous insertion, such as when necessary to penetrate areas of thick epidermis, for instance, on the hands or feet, or animal hide. For instance, the cutting edge 71 can be shaped into a point or semi-point, which can initially pierce and progressively enlarge an implantation site. Similarly, the cutting edge 81 can be shaped into a rounded or curved edge, which can also progressively enlarge an implantation site, but without initial piercing. In addition, the cutting edge 91 upwardly curved or angled, which can help shape the implantation site to more closely follow the contours of the object to be implanted. Other cutting edge shapes are possible. Moreover, dissecting tools could be used in addition to or in lieu of the progressive cutting edges, such as a flat or shaped dissecting tool.

Figure 11:
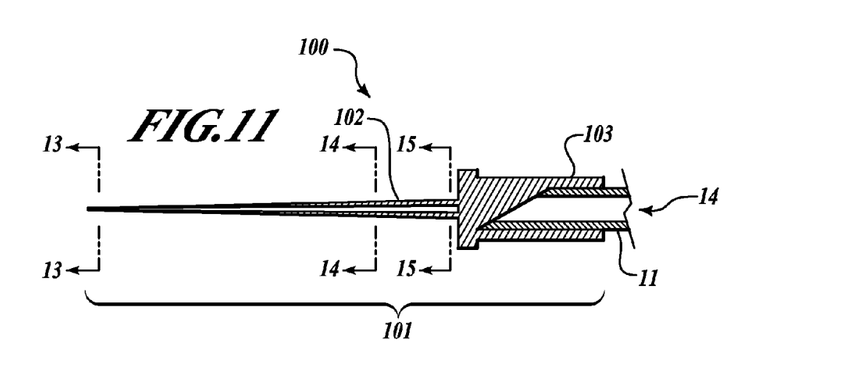
FIG. 11 is a longitudinal cross-sectional view of a subcutaneous implantation instrument in accordance with a further embodiment.

FIG. 11 is a longitudinal cross-sectional view of a subcutaneous implantation instrument 100 in accordance with a further embodiment. A dissecting tool assembly 101 is removably affixed to the distal end of the incising shaft 11 with a coupling sheath 103, which can be constructed as an over sleeve frictionally fit over the incising shaft 11, a snapoff assembly that detaches from the incising shaft 11 by twisting or distal movement, or some other type of coupling that is non-integral to the incising shaft 11. The dissecting tool assembly 101 includes a needle tip 102 that defines a lumen that internally interfaces to the bore opening 14 of the incising shaft 11 and which can be used to inject a local anesthetic agent or other liquid or semi-liquid substance into the implantation site. The needle tip 102 also progressively defines a pair of cutting blades along each outward facing edge.

Figure 12:
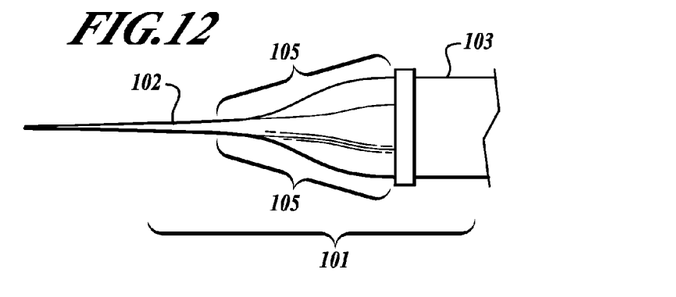
FIG. 12 is a top plan view of the subcutaneous implantation instrument of FIG. 11.

FIG. 12 is a top plan view of the subcutaneous implantation instrument 100 of FIG. 11. The cutting blades are oriented longitudinally and planar to the cutting edge 13 of the incising shaft 11. The cutting blades provide cutting edges 105, which gradually increase the width of the incision made when the implantation instrument 100 is inserted subcutaneously. The cutting edges 105 can be straight, concave, convex, or a combination thereof.

Figure 13:
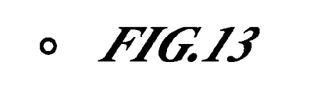
FIGS. 13-15 are transverse cross-sectional views of the dissecting tool assembly of FIG. 11.
Figure 14:
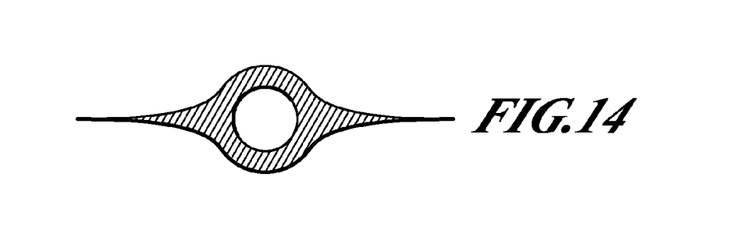
Figure 15:
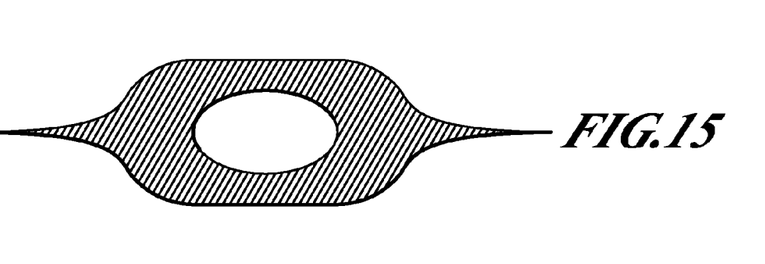

FIGS. 13-15 are transverse cross-sectional views of the dissecting tool assembly 101 of FIG. 11. On a distal end, the needle tip 102 internally defines a lumen of approximately 16 French, which tapers outwardly to a larger diameter bore and substantially non-circular bore of approximately 30 gauge on the proximal end. The cutting edges 105 become increasingly pronounced towards the proximal end of the needle tip 102. Other lumen, bore sizes, and cutting edge arrangements are possible.

Figure 16:
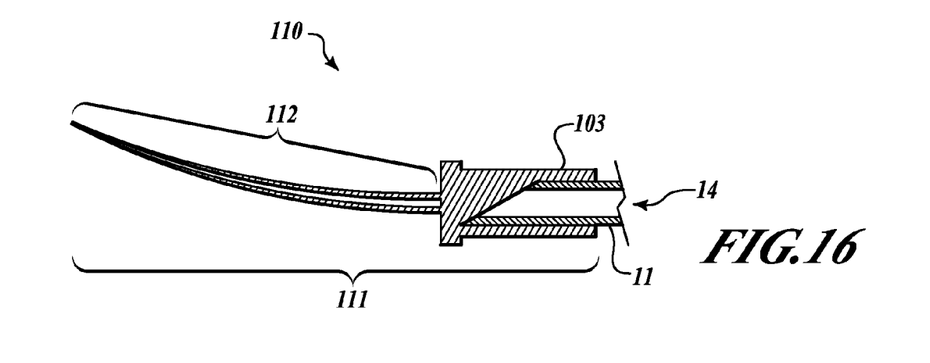
FIG. 16 is a longitudinal cross-sectional view of a subcutaneous implantation instrument in accordance with a still further embodiment.

FIG. 16 is a longitudinal cross-sectional view of a subcutaneous implantation instrument 110 in accordance with a still further embodiment. A curved dissecting tool assembly 111 bends in a gradual arc 112 upwardly towards the incising blade 11 to facilitate implantation. The curved dissecting tool assembly 111 can be used with either the straight incising shaft 11 or curved incising shaft 24. The curvature enables the implantable object to be more easily oriented parallel to the surface of the skin, rather than at an angle.

Figure 17:
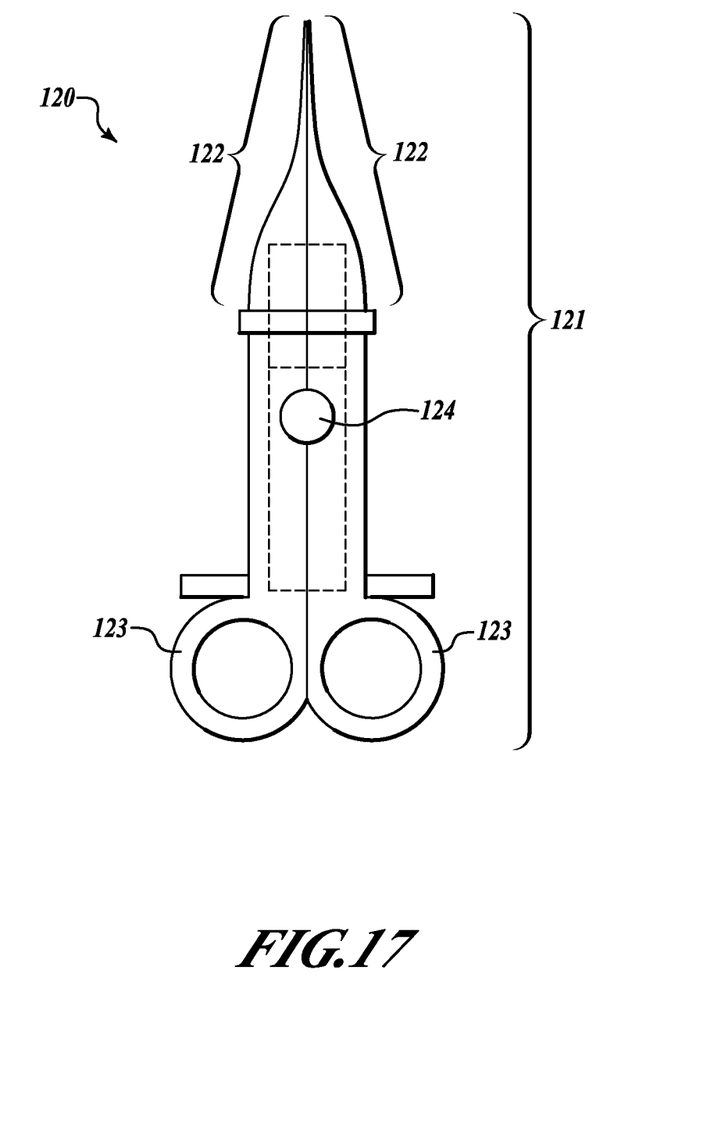
FIG. 17 is a top plan view of a subcutaneous implantation instrument in accordance with an even further embodiment.

FIG. 17 is a top plan view of a subcutaneous implantation instrument 121 in accordance with an even further embodiment. A scissored dissecting tool assembly 122 is divided into two halves, which are each attached to a handle 123 that is pivotably mounted 124, in the manner of a pair of scissors. The handles 123 can be operated outwardly to cause the distal end of the scissored dissecting tool assembly 122 to open and longitudinally cut into the surrounding tissues, thereby widening the implantation site. Once the implantation site has been suitably cleared, the scissored dissecting tool assembly 122 remains open and the plunger assembly 20 is progressive urged distally to insert the implantable object. The scissored dissecting tool assembly 122 can be straight or curved to facilitate implantation. Other forms of scissored dissecting tool assemblies are possible.

Figure 18:
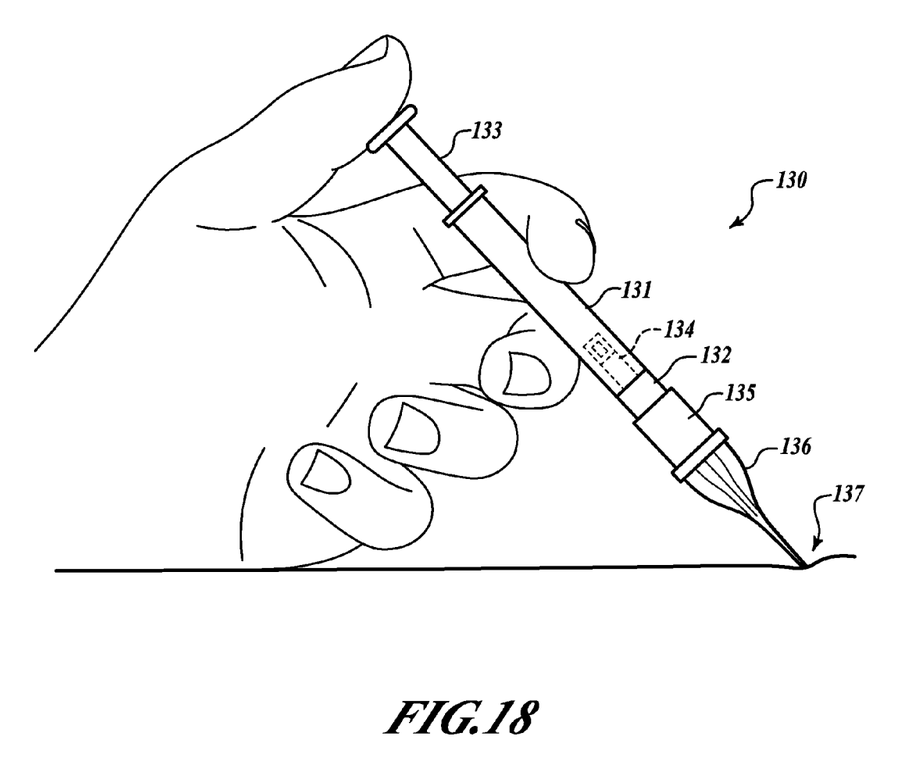
FIGS. 18-20 are perspective diagrams showing a method of use for the subcutaneous implantation instrument in accordance with one embodiment.
Figure 19:
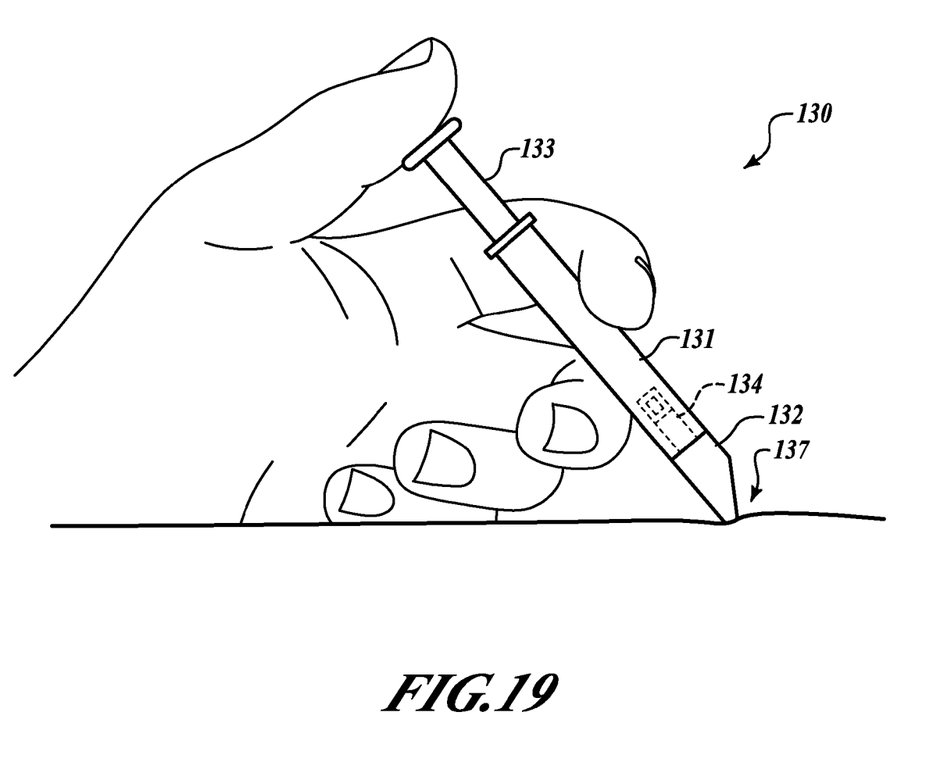
Figure 20:
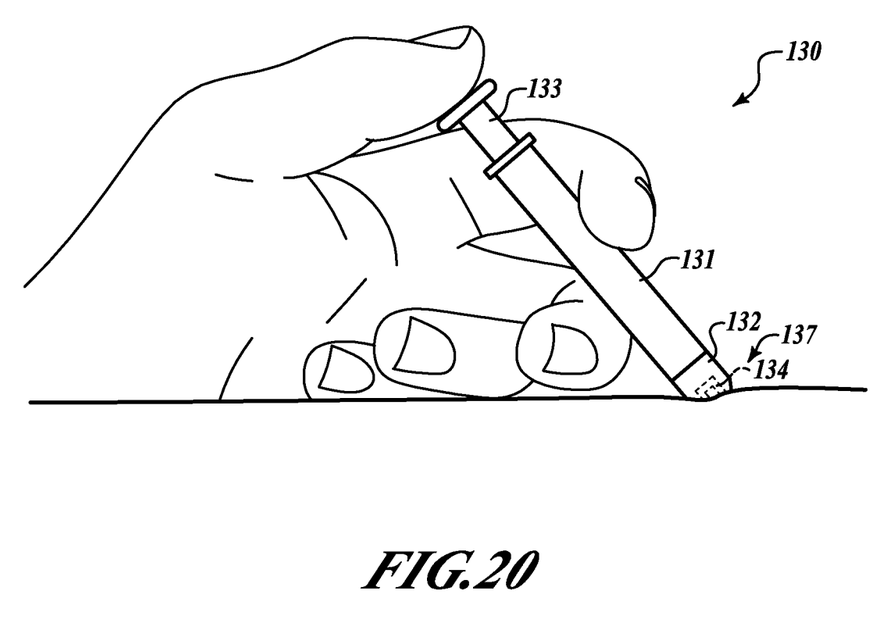

FIGS. 18-20 are perspective diagrams showing a method of use for the subcutaneous implantation instrument 121 in accordance with one embodiment. Referring first to FIG. 18, the subcutaneous implantation instrument 130 can be used for out-patient or non-surgical subcutaneous insertion of an implantable object, such as an implantable sensor, medical device, or solid material. The implantation instrument 10 enables the subcutaneous insertion of implantable objects and devices, such as sensors, without an operating room or special procedures room. The implantation instrument 10 reduce insertion of implantable objects and devices having non-conforming shapes to be the functional equivalent of an injection.

The subcutaneous implantation instrument 130 can be sold or marketed as part of a package that combines an implantable object 134 with the subcutaneous implantation instrument 130, particularly where the subcutaneous implantation instrument 130 is provided as a single-use disposable unit. Thus, the subcutaneous implantation instrument 130 can be offered with an implantable 134 object already disposed within the syringe body 131, with the entire package sealed ready for use inside sterile packaging (not shown). Alternatively, the subcutaneous implantation instrument 130 can be offered in combination with an implantable object 134 that is packaged separately.

At the outset of the procedure, an implantation site 137 can be locally anesthetized using the subcutaneous implantation instrument 130 by fitting the incising shaft 132 with a dissecting tool assembly 136, as provided in a further embodiment, described above with reference to FIG. 11 et seq. The coupling sheath 103 of the dissecting tool assembly 136 removably fits over the distal end of the incising shaft 132. The implantation site 137 is cleaned and sterilized and the needle tip 102 is inserted subcutaneously. The needle tip 102 and cutting blades on the dissecting tool assembly 136 form a progressively larger opening as the subcutaneous implantation instrument 130 is pressed downward through the skin. The plunger assembly 133 is then pressed distally to inject a local anesthetic agent into the subcutaneous implantation site.

Referring next to FIG. 19, the dissecting tool assembly 136 is withdrawn from the implantation site 137 and removed from the incising shaft 132, thereby exposing the cutting edge of the incising shaft 132. The bare incising shaft 132 is inserted into the previously cleared implantation site 137 and pressed downward. Depending upon the configuration of the cutting edges 105 of the dissecting tool assembly 136, the cutting edge of the incising shaft 132 may only need to enlarge the opening, rather than clearing a full width opening.

Referring finally to FIG. 20, downward movement of the subcutaneous implantation instrument 130 is stopped when the appropriate depth for implantation has been reached and, if necessary, is urged slight back to clear the incising shaft 137 from the actual subcutaneous implantation site. The plunger assembly 133 is again pressed distally to deploy the implantable object 134 into the incising shaft 134 and thence to insert the implantable object 134 into the subcutaneous implantation site. The incising shaft 132 is withdrawn and the wound is appropriately dressed to complete the implantation procedure. Through use of the method, the subcutaneous sensor insertion of implantable objects and devices, such as sensors, having non-conforming shapes is thereby reduced to be the functional equivalent of an injection.

While the invention has been particularly shown and described as referenced to the embodiments thereof, those skilled in the art will understand that the foregoing and other changes in form and detail may be made therein without departing from the spirit and scope of the invention.

What is claimed is:

1. A subcutaneous implantation instrument with a scissored dissecting tool assembly, comprising:
    an incising shaft longitudinally defining a substantially non-circular bore continuously formed to communicatively receive an implantable object and further comprising a beveled cutting blade formed on a distal end;
    a dissecting tool assembly, comprising:
        a longitudinally split needle tip forming a pair of blades with cutting edges progressively defined outwardly from the needle tip;
        a pair of handles that are each attached to one of the blades at a distal end of each handle and pivotably coupled and disposed for operation transverse to the needle tip, wherein the dissecting tool assembly is removably affixable to the distal end of the incising shaft; and
    a delivery mechanism longitudinally defining a substantially non-circular bore continuously formed to deploy the implantable object into the incising shaft.

2. A subcutaneous implantation instrument in accordance with claim 1, wherein the blades are formed with at least one of straight, concave, and convex surfaces.

3. A subcutaneous implantation instrument in accordance with claim 1, wherein the longitudinally split needle tip is formed into a curve arced towards the incising shaft.

4. A method for constructing a subcutaneous implantation instrument with a scissored dissecting tool assembly, comprising:
    fashioning an incising shaft to longitudinally define a substantially non-circular bore continuously formed to communicatively receive an implantable object and further comprising a beveled cutting blade formed on a distal end;
    assembly a dissecting tool assembly, comprising:
        providing a longitudinally split needle tip to form a pair of blades with cutting edges progressively defined outwardly from the needle tip;
        including a pair of handles that are each attached to one of the blades at a distal end of each handle and pivotably coupled and disposed for operation transverse to the needle tip, wherein the dissecting tool assembly is removably affixable to the distal end of the incising shaft; and
    providing a delivery mechanism to longitudinally define a substantially non-circular bore continuously formed to deploy the implantable object into the incising shaft.

5. A method in accordance with claim 4, wherein the blades are formed with at least one of straight, concave, and convex surfaces.

6. A method in accordance with claim 4, wherein the longitudinally split needle tip is formed into a curve arced towards the incising shaft.

* * * * *